United States Patent [19]

Dear et al.

[11] 4,081,399
[45] Mar. 28, 1978

[54] PROCESS FOR THE PREPARATION OF CONCENTRATED SOLUTIONS OF FLUORINATED AMPHOTERIC SURFACTANTS

[75] Inventors: Robert Ernest Arthur Dear, Mount Kisco; Thomas W. Cook, Yorktown Heights, both of N.Y.

[73] Assignee: Ciba-Geigy Corporation, Ardsley, N.Y.

[21] Appl. No.: 615,339

[22] Filed: Sep. 22, 1975

[51] Int. Cl.$^2$ .............................................. B01F 17/28
[52] U.S. Cl. ................. 252/356; 260/534 S; 260/561 S; 260/609 B; 260/609 R
[58] Field of Search ............ 260/534 S, 609 R, 609 B, 260/561 S; 252/356

[56] References Cited

U.S. PATENT DOCUMENTS

| | | | |
|---|---|---|---|
| 2,368,067 | 1/1945 | Lynch | 260/534 S |
| 3,003,954 | 10/1961 | Brown | 252/356 |
| 3,172,910 | 3/1965 | Bruce | 260/561 S |
| 3,211,747 | 10/1965 | Johnson | 260/534 R |
| 3,759,981 | 9/1973 | Hager et al. | 252/356 |
| 3,833,651 | 9/1974 | Ouchi et al. | 260/534 S |
| 3,947,493 | 3/1976 | Balme et al. | 260/534 E |
| 3,950,542 | 4/1976 | Kalopissis et al. | 260/534 S |

OTHER PUBLICATIONS

Riddick et al., "Organic Solvents", 3rd ed. (1970), also Techniques of Chemistry, vol. II, pp. 446, 447, 467, 460, 6.
Monick, "Alcohols", 1968, pp. 282, 283, 284, 285, 286, 306.

*Primary Examiner*—Joseph E. Evans
*Attorney, Agent, or Firm*—Nestor W. Shust

[57] ABSTRACT

The invention is directed to a process for the preparation of concentrated solutions of fluorinated surfactants of the formula

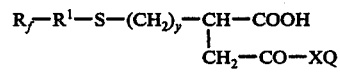

wherein $R_f$ is a perfluoroalkyl or perfluoroalkoxy-perfluoroalkyl group, $R^1$ is a branched or straight chain alkylene, alkylenethioalkylene, alkyleneoxy-alkylene or alkyleneiminoalkylene group, X is oxygen or an amino group, Q is an organic group containing at least one amino group and y is zero or 1, said process comprising (a) reacting an aqueous solution of an amine with an anhydride previously dissolved in an anhydrous water miscible organic solvent, dissolved in an anhydrous water miscible organic solvent, and (b) reacting the intermediate obtained from the first reaction with an $R_f$-thiol in the presence of a non-reactive water miscible thiol solvent.

4 Claims, No Drawings

PROCESS FOR THE PREPARATION OF CONCENTRATED SOLUTIONS OF FLUORINATED AMPHOTERIC SURFACTANTS

BACKGROUND OF THE DISCLOSURE

The fluorinated amphoteric surfactants represented by the formulas below are described in greater detail in copending application of K. Mueller, Ser. No. 538,432, filed Jan. 3, 1975. When used as surfactants such compounds usually do not need to be isolated but are preferably used in a concentrated solution. The greater the solid content of such surfactants in a solution, the greater variety in final formulations (such as aqueous film forming foams) can be obtained. Said copending application discloses methods of preparation of concentrated solutions of such surfactants, but these methods produce solutions of at most only about 30% solids. The process of the instant invention is capable of producing solutions containing about 60% solids. Additionally, in known processes disclosed in Ser. No. 538,432, solid maleic anhydride is added to an aqueous solution of an amine which results in some hydrolysis to maleic acid which is an undesirable by product.

The hydrolysis of maleic anhydride can be eliminated by a process disclosed in Canadian Patent 828,195 which teaches the use of a nonaqueous solvent for the addition of maleic anhydride. The solvent has to be immiscible with water and not a solvent for the reaction product, and it must be removed before the second step (mercaptan addition) is carried out. This effectively minimizes diacid formation since the anhydride is dissolved, e.g. in methylene chloride, and is extracted from solution by the more reactive amine and not by water. However, in this process the solvent must be removed before a further reaction is carried out, which is tedious, time consuming and expensive which makes this approach commercially impractical. Furthermore, the process in said Canadian patent deals only with the first step of the reaction involved in the preparation of the surfactants and therefore in no way suggests how to prepare a solution having a higher solid content of the surfactant.

DETAILED DISCLOSURE

This invention deals with the preparation of a concentrated water miscible solution of fluorinated amphoteric surfactants. Such concentrates are useful in the formulation of aqueous film forming foams (AFFF) as discussed in greater detail in copending application Ser. No. 538,432. The compounds obtained by the instant process are not isolated but are used directly in solution. If said surfactants are in a highly concentrated form, then a greater variety in formulation can be achieved. Therefore, the critical object of this invention is to prepare solutions containing as high solids content as possible. The further advantage of the present process is the reduction in the production of undesirable by-products, such as maleic acid and its addition products.

More specifically, the present invention is directed to a process for the preparation of a concentrated solution of fluorinated amphoteric surfactants represented by the formulae

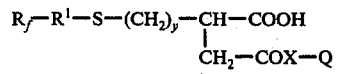
$$R_f-R^1-S-(CH_2)_y-CH-COOH$$
$$|$$
$$CH_2-COX-Q$$
I and its isomer

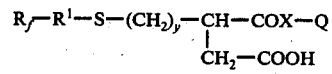
$$R_f-R^1-S-(CH_2)_y-CH-COX-Q$$
$$|$$
$$CH_2-COOH$$
II wherein $R_f$ is straight or branched chain perfluoroalkyl of 1 to 18 carbon atoms or said perfluoroalkyl substituted by perfluoroalkoxy of 2 to 6 carbon atoms, $R^1$ is branched or straight chain alkylene of 1 to 12 carbon atoms, alkylenethioalkylene of 2 to 12 carbon atoms, alkyleneoxyalkylene of 2 to 12 carbon atoms or alkyleneiminoalkylene of 2 to 12 carbon atoms where the nitrogen atom contains as a third substituent, hydrogen or alkyl of 1 to 6 carbon atoms, y is 1 or zero, X is oxygen or —NR, wherein R is hydrogen, lower alkyl of 1 to 6 carbon atoms, hydroxyalkyl of 1 to 6 carbon atoms, or R together with Q forms a piperazine ring, and Q is an aliphatic amino group of the formula

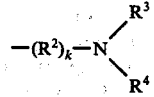
$$-(R^2)_k-N\begin{matrix}R^3\\R^4\end{matrix}$$
(Ia)

wherein $R^2$ is a linear or branched alkylene of 2 to 12 carbon atoms, oxygen or sulfur interrupted linear or branched alkylene of up to 60 carbon atoms, or hydroxyl substituted alkylene;

k is 1 or zero, with the proviso, that if X is oxygen, k is 1;

$R^3$ and $R^4$ are independently of each other hydrogen, alkyl group, substituted alkyl group of 1 to 20 carbon atoms; phenyl group, an alkyl or halogen substituted phenyl group of 6 to 20 carbon atoms, polyethoxy or polypropoxy group of 2 to 20 alkoxy units with the proviso that if X is oxygen, $R^3$ and $R^4$ are not hydrogen; said process comprising (a) reacting an aqueous solution of an amine with an anhydride previously dissolved in an anhydrous, non-reactive water miscible organic solvent, and (b) reacting the product obtained in the previous (first) step with an $R_f$-thiol in the presence of a non-reactive, water miscible thiol solvent.

In a preferred embodiment the integer y is zero and the groups $R^3$ and $R^4$ are lower alkyl of 1 to 4 carbons and most preferable methyl groups.

The solvents in which the anhydride can be dissolved must be non-reactive and miscible with water but must be anhydrous at the time the anhydride is dissolved therein. Illustrative examples of such useful solvents are tetramethylene sulfone (tetrahydrothiophene-1,1-dioxide), acetone, methyl ethyl ketone, dimethyl formamide, dimethylacetamide, hexamethylphosphoramide, N-methyl pyrrolidone, acetonitrile, tetrahydrofuran, ethylene glycol dimethylether (glyme), diethylene glycol dimethylether (diglyme), triethylene glycol dimethylether (triglyme), diethyl carbitol, dimethylsulfoxide, dioxane and the like. Tetramethylene sulfone is most preferable because of its high boiling point (nonflammability), low toxicity and high solvent power. Although it is not critical to this invention how much solvent is used, it is preferable that only enough solvent be employed to dissolve the anhydride. Besides being economical, this will produce a composition containing the highest possible solids content.

The first step of the reaction is exothermic and therefore should be carried out at a low temperature, such as 0° to 35° C and preferably at 10° to 25° C. In the second step of the reaction, it is preferable, though not critical, to add to the reaction product from the first step a nonreactive, water miscible thiol solvent and thereafter to add to this reaction mixture the $R_f$-thiol. However, the reaction could also be carried out if the $R_f$-thiol were first dissolved in the solvent and the solution then added to the reaction mixture. This reaction is carried out at a temperature between 20° and 100° C, and preferably between 40° and 60° C.

Illustrative examples of water miscible solvents of $R_f$-thiol are alcohols such as methanol, ethanol, n-propanol, isopropanol, n- and isobutanol, butyl carbitol, ethylene glycol, propylene glycol 1,2 and 1,3, butylene glycol 1,3 and 1,4, hexylene glycol, 2,2-diethyl-1,3-propanediol, 1,4-cyclohexanedimethanol (cis and trans) and the like; ethers such as glycol ethers (Dowanols, Carbitols and Cellosolves), ethylene glycol monomethyl ether, ethylene glycol dimethyl ether, ethylene glycol monoethyl ether, ethylene glycol monobutyl ether, diethylene glycol, triethylene glycol, tetraethylene glycol, diethylene glycol, monoethyl ether, diethylene glycol monoethyl ether, diethylene glycol diethyl ether, diethylene glycol monobutyl ether, tetrahydrofuran and the like; ketones such as acetone, methyl ethyl ketone, methyl n-propyl ketone, chloroacetone, diacetyl, acetyl acetone, mesityl oxide and the like; N-methyl pyrrolidone, dimethylformamide, acetonitrile, dioxane and the like. Preferable solvents are water soluble sec- and tert-alcohols. The most preferable solvent is hexylene glycol.

The ratio of the water miscible thiol solvent to water is a critical factor in this invention if a homogeneous liquid composition is to be obtained. If an insufficient amount of the solvent is employed, the resulting composition is a gel. If an excess of the solvent is used, a nonhomogeneous product results (2 layers). The specific ratio of the thiol solvent to water also depends on the solubility of the thiol, the solubility of the surfactant end-product and the specific anhydride solvent employed. For example, if tetramethylene sulfone is used as the anhydride solvent and hexylene glycol is used as the thiol solvent, the acceptable ratio of water to hexylene glycol is from 1:0.75 to 1:1.2.

Since it is clear from the above that the specific ratio of the thiol solvent to water depends on many factors, it is impossible for one to predict the acceptable ratio for a particular solvent. A routine method to determine the acceptable ratios for various solvents is to carry out a series of trial reactions varying the amounts of water and of the two solvents and observe whether the resulting product is homogeneous, gelled or heterogeneous. If the product is a gel, then the amount of the thiol solvent should be increased and the amount of water decreased. If the product is heterogeneous, the thiol solvent should be decreased and the amount of water increased. When the above adjustments are made the anhydride solvent should be kept constant which, as noted earlier, should be employed in minimum amounts.

The preferred scope of the compounds prepared by the process of this invention is stated above where Q is defined as an aliphatic amino group. Q, however, can be additionally a nitrogen containing group selected from (1)

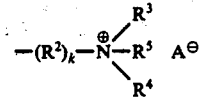
(1b)

and

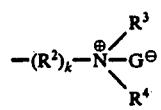
(1c)

wherein
$A^\ominus$ is any anion which forms an ammonium salt of the formula $NH_4^\oplus A^\ominus$.

Anion $A^\ominus$ is derived from alkyl halides, benzene or chlorobenzene sulfonate esters of alkyl alcohols and methyl and ethyl sulfates. $A^\ominus$ is preferably $Cl^\ominus$, $Br^\ominus$, $CH_3CH_2OSO_3^\ominus$.

$R^5$ is hydrogen, an alkyl group or hydroxyalkyl group, aralkyl or groups of the formula —$(CH_2)_n$—COO-alkyl, said alkyl group having 1 to 18 carbons. Preferably, $R^5$ is methyl, ethyl, propyl, butyl or benzyl.

$G^\ominus$ is a group selected from the groups

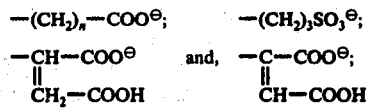

wherein n is 1 to 5;
(2) cyclic amino groups selected from

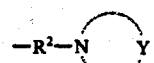
(2a)

(2b)

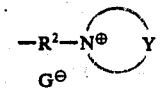
(2c)

wherein Y is a diradical group of the formulae:

$$-(CH_2)_4-$$
$$-(CH_2)_5-$$
$$-(CH_2)_2-O-(CH_2)_2-$$
$$-(CH_2)-CH-N-(CH_2)_2-$$
$$\phantom{-(CH_2)-CH-N}|\phantom{-(CH_2)}|$$
$$\phantom{-(CH_2)-CH-N}R^7\phantom{-(C}R^8$$

wherein $R^2$, $R^5$, $A^\ominus$ and $G^\ominus$ are as defined above,
$R^7$ and $R^8$ are independent hydrogen, a lower alkyl or hydroxy-lower alkyl group of 1 to 6 carbon atoms, with the proviso that if X is oxygen, $R^8$ cannot be hydrogen.
(3) aromatic amino groups selected from

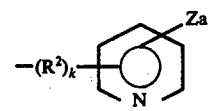
(3a)

(3b)

$$-(R^2)_k-\underset{\underset{R^5}{|}}{\underset{N^\oplus}{\bigcirc}}\diagdown Za \quad A^\ominus \quad \text{and}$$

(3c)

$$-(R^2)_k-\underset{\underset{G^\ominus}{N^\oplus}}{\bigcirc}\diagdown Za$$

(4) fused-ring aromatic amino group selected from (4a)

$$-(R^2)_k-\underset{N}{\bigcirc\bigcirc}\diagup^{Za}\diagdown_{Zb}$$

(4b)

$$-(R^2)_k-\bigcirc\underset{\underset{R^5}{|}}{\underset{N^\oplus}{\bigcirc}}\diagup^{Za}\diagdown_{Zb} \quad A^\ominus$$

and (4c)

$$-(R^2)_k-\bigcirc\underset{\underset{G^\ominus}{N^\oplus}}{\bigcirc}\diagup^{Za}\diagdown_{Zb} \quad A^\ominus$$

wherein
Z is halogen or methyl,
a + b is an integer from 0–3; and
(5) a heterocyclic amino group of the formula

| (5a) | —(R²)ₖ—E |    |
|------|----------|----|
| (5b) | —(R²)ₖ—E⁺—R⁵ | A⁻ |
| (5c) | —(R²)ₖ—E⁺—G⁻ |    | where k is one or zero and

E is selected from N-hydroxyalkyl or N-aminoalkyl, substituted pyrrole, pyrazole, imidazole, triazole, indole or indazole, hydroxyalkyl and aminoalkyl ring-substituted pyridazine, pryimidino, pyrazino or quinoxalino.

The compounds represented above by formulae I and II where Q is of structures (1a), (2a), (3a), (4a) or (5a) exist in solution in the form of their inner salts, having the general structures $$R_f-R^1-S-(CH_2)_y-\underset{\underset{CH_2-COX-\overset{\oplus}{Q}H}{|}}{CH-COO^\ominus} \quad \text{Ia}$$

and $$R_f-R^1-S-(CH_2)_y-\underset{\underset{CH_2-COO^\ominus}{|}}{CH-COX-\overset{\oplus}{Q}H} \quad \text{IIa}$$

and thus are amphoteric surfactants.

The anhydrides employed in the instant process are maleic and itaconic anhydrides. The amines and the $R_f$ thiol compounds of the formula $R_f-R^1-SH$, wherein $R^1$ is alkylene of 1 to 16 carbon atoms and $R_f$ is perfluoroalkyl, which are also employed instantly are fully disclosed and exemplified in said copending application Ser. No. 538,432, which disclosure is incorporated herein by reference.

The surfactant compositions obtained by the process of this invention are soluble in water or water/co-solvent mixtures and are directly useful in preparing aqueous film forming foams (AFFF) as disclosed in copending application Ser. No. 561,393, filed Mar. 24, 1975, now U.S. Pat. No. 4,042,522, whose disclosure of utility is incorporated herein by reference.

The examples below are presented for illustrative purposes only and are not intended to limit in any way the scope of the invention which is defined by the Claims.

EXAMPLE 1

N-(N',N'-Dimethylaminopropyl)-2(and 3)-(1,1,2,2-tetrahydroperfluoroalkylthio) succinamic acid Crushed maleic anhydride (210 g; 2.14 mole) was added in 10 g. portions over a 30 minute period, to N,N-dimethylpropane-1,3-diamine (218 g; 2.14 mole) in a 12 liter flask containing 428 g. distilled water. The flask was equipped with a stirrer, thermometer and nitrogen inlet and was cooled with an external ice bath to maintain the interior temperature between 10° and 20° C. After the final addition of maleic anhydride, cooling was discontinued and the solution was stirred at 25° for 2 hours. Hexylene glycol (2-methylpentane-2,4-diol) (1280 g.) was added to the above aqueous solution, followed by 1,1,2,2-tetrahydroperfluoroalkyl mercaptan (938 g, 2.04 mole). (In this and other examples, unless otherwise specified, perfluoroalkyl refers to a group $C_nF_{2n+1}$ where n is principally $C_6$, $C_8$, and $C_{10}$, in the approximate ratio of 1:2:1.) Over a 30 minute period a gradual thickening of the reaction mixture was noted together with a temperature increase of 3° to 4° C. At this stage the exotherm was controlled by application of a water bath so that the reaction temperature was maintained between 25° and 30° C. After 3½ hours no unreacted mercaptan was detected by GLC. The resulting white suspension was diluted to a solution containing 30 percent solids with 1480 g. distilled water and then clarified by pressure filtration.

The composition of the final solution was:
% solids — 30.0
% water — 41.9
% hexylene glycol — 28.1 where the solids were N-(N',N'-dimethylaminopropyl)-2(and 3)-1,1,2,2-tetraphydroperfluoroalkylthio) succinamic acid.

Impurities in the aqueous solution were maleic acid and 2-(1,1,2,2-tetrahydroperfluoroalkylthio) succinic acid.

EXAMPLE 2

N-(N',N'-Dimethylaminopropyl)-2(and-3)-(1,1,2,2-tetrahydroperfluoroalkylthio) succinamic acid Maleic anhydride (101.9 g; 1.04 mole) was dissolved in 200 g. of dichloromethane, with stirring and warming to 25° C. This solution was added slowly (30 to 60 minutes) to a chilled (10° C) solution of N,N-dimethylpropane-1,3-diamine (106.1 g; 1.04 mole) in 208 g. deionized water. The reaction temperature was maintained at 10° to 25° with an ice bath. After complete addition the mixture was stirred at 25° for 1 hour, then allowed to separate into two liquid layers. The lower (dichloromethane) layer was drawn off and residual solvent in the aqueous layer was removed by pumping the stirred solution at 25° C and 15 mm Hg for 1 hour. Following this, hexylene glycol (192 g.) and 1,1,2,2-tetrahydroperfluoroalkyl mercaptan (392 g, 0.83 mole) were added to the aqueous solution and stirred for 4 hours at 25°-30° C. The reaction was complete in that time to give 1000 g. of clear solution containing 600 g. solids. The molar ratios of the reactants used were such that the product consisted of 93.2 weight percent N-(N',N'-dimethylaminopropyl-2(and-3)-(1,1,2,2-tetrahydroperfluoroalkylthio) succinamic acid and 6.8 weight percent N-(N',N'-dimethylaminopropyl) maleamic acid. The composition of the solution was % solids — 60.0
% water — 20.8
% hexylene glycol — 19.2

Example 2 and Examples 2A, 2B and 2C demonstrate the need for a certain minimum proportion of water to be present in order to achieve a homogeneous solution containing 60 percent solids.

EXAMPLES 2A – 2C

Using the procedure described in Example 2, the following reactions were carried out:

| Reactants | | Examples | | |
|---|---|---|---|---|
| | | 2A | 2B | 2C |
| Maleic anhydride | (g) | 12.24 | 12.24 | 12.24 |
| N,N-dimethylpropane-1,3-diamine | (g) | 12.75 | 12.75 | 12.75 |
| Water | (g) | 25.00 | 25.00 | 24.03 |
| Hexylene glycol | (g) | 75.00 | 50.00 | 24.03 |
| $R_fCH_2CH_2SH$ | (g) | 47.11 | 47.11 | 47.11 |
| Ratio $H_2O$:Hg | | 1:3 | 1:2 | 1:1 |
| % Solids | | 42 | 49 | 60 |
| Appearance of product | | 2 layers | 2 layers | homogeneous |

The product of Example 2A became homogeneous after the addition of a further 50 g. water, bringing the solids content to 32 percent and the water: hexylene glycol ratio to 1:1. The product of Example 2B similarly became homogeneous after the addition of a further 25 g. water, making a product containing 42 percent solids and a 1:1 ratio of water to hexylene glycol.

EXAMPLE 3

N-(N',N'-Dimethylaminopropyl)-2(and-3)-(1,1,2,2-tetrahydroperfluoroalkylthio) succinamic acid Maleic anhydride (101.7 g; 1.04 mole) was dissolved in 66.9 g. of tetramethylene sulfone (tetrahydrothiophene-1,1-dioxide) with stirring and warming to 25°. This solution was added slowly (30 to 60 minutes) to a chilled solution (10° C) of N,N-dimethylpropane-1,3-diamine (106.0 g; 1.04 mole) in 175 g. water. The temperature of the exothermic reaction was maintained at 10° to 25° C with an ice bath. After complete addition the mixture was stirred at 25° C for 1 hour. Then 158 g. hexylene glycol and 1,1,2,2-tetrahydroperfluoroalkyl mercaptan (392.4 g; 0.83 mole) were added to the above solution and stirred at 25° to 50° C for 1 hour, after which no further mercaptan was detected by gas chromatography. The resulting product was a clear solution (b 1000 g.) containing 600 g. solids as detailed in Example 2. The composition of the solution was % solids — 60.0
% tetramethylene sulfone — 6.7
% hexylene glycol — 15.8
% water — 17.5

Use of a water soluble solvent for the maleic anhydride eliminates the need for the expensive and time consuming removal of solvent as in Example 2. No diacid impurities were evident using this procedure.

EXAMPLES 4 – 11

Following the procedure described in Example 3, tetramethylene sulfone was used as a solvent for maleic anhydride (60 percent solids in tetramethylene sulfone, TMS), and the ratios of hexylene glycol:water were varied over a wide range to show the useful limits of the process. The examples also show the effect of increasing amounts of hexylene glycol on the speed of the reaction. In each example 20.2 g. of maleic anhydride were dissolved in 13.5 g. tetramethylene sulfone (TMS) and allowed to react with 21.05 g. N,N-dimethylpropane-1,3-diamine, followed by 78.6 g. 1,1,2,2-tetrahydroperfluoroalkyl mercaptan. All reactions were initially heated to 45° and then allowed to find their own final temperature.

TABLE I

| EXAMPLE | 4 | 5 | 6 | 7 | 8 | 9 | 10 | 11 |
|---|---|---|---|---|---|---|---|---|
| $H_2O$ used (g) | 54.92 | 49.95 | 44.95 | 39.95 | 36.46 | 34.96 | 33.46 | 29.97 |
| Hexylene glycol used (g) (HG) | 11.58 | 16.58 | 21.58 | 26.59 | 30.07 | 31.57 | 33.07 | 36.56 |
| Composition of Product: | | | | | | | | |
| % solids | 59.97 | 59.96 | 59.96 | 60.00 | 59.96 | 59.96 | 59.96 | 59.96 |
| % TMS | 6.74 | 6.74 | 6.74 | 6.70 | 6.74 | 6.74 | 6.74 | 6.74 |
| % $H_2O$ | 27.49 | 25.00 | 22.50 | 19.99 | 18.25 | 17.50 | 16.75 | 15.00 |
| % HG | 5.80 | 8.30 | 10.80 | 13.31 | 15.05 | 15.80 | 16.55 | 18.30 |
| Reaction time | ca 150 min | ca 90 min | ca 55 min | 42 min | 26 min | 20 min | 17 min | 12 min |
| Appearance of Final Product | firm gel | firm gel | firm gel | viscous gel | clear liquid | clear liquid | clear liquid | cloudy* liquid (2 layers) |
| Viscosity (cps) at 25° C | not measurable | | | | 855 | 840 | 775 | 720 |

*Became clear after several days

EXAMPLES 12 – 14

These examples illustrate the use of N-methylpyrrolidone as a solvent for maleic anhydride, and show that the correct water/hexylene glycol ratio must be used to achieve solution of the final product. In each example 102 g. maleic anhydride were dissolved in 43-7 g. N-methylpyrrolidone (70 percent solids in N-methylpyrrolidone-NMP) and allowed to react with 106.3 g. N,N-dimethylpropane-1,3-diamine, followed by 392.4 g. 1,1,2,2-tetrahydroperfluoroalkyl mercaptan.

TABLE II

| Example | 12 | 13 | 14 |
|---|---|---|---|
| $H_2O$ used (g) | 156.8 | 178.4 | 200.0 |
| Hexylene glycol used (g) (HG) | 200.0 | 178.4 | 156.8 |
| Composition of product: | | | |
| % solids | 60.00 | 60.00 | 60.00 |
| % NMP | 4.36 | 4.36 | 4.36 |
| % $H_2O$ | 15.66 | 17.82 | 19.98 |
| % HG | 19.98 | 17.82 | 15.66 |

TABLE II-continued

| Example | 12 | 13 | 14 |
|---|---|---|---|
| Appearance of final product | 2 phases | 2 phases (cloudy) | clear solution |

EXAMPLES 15 – 18

These examples show the utility of other water miscible solvents for maleic anhydride. In each case 50 g. maleic anhydride was dissolved in the solvent to give a solution of the concentration noted. This was not a saturated solution, but as concentrated as is practical. This solution was added to 52.1 g. N,N-dimethylpropane-1,3-diamine in 100 g. water. The amount of hexylene glycol added was governed by the amount of solvent used and is shown in the table. Finally, 193.9 g. 1,1,2,2-tetrahydroperfluoroalkyl mercaptan was added to provide a solution containing N-(N',N'-dimethylaminopropyl)-2(and 3-)-(1,1,2,2-tetrahydroperfluoroalkylthio) succinamic acid.

TABLE III

| Example | 15 | 16 | 17 | 18 |
|---|---|---|---|---|
| Solvent* | acetone | diglyme | DMF | DMAC |
| % Maleic anhydride in Solution | 70 | 50 | 70 | 70 |
| Composition of product: | | | | |
| % solids | 60.00 | 60.00 | 60.00 | 60.00 |
| % solvent | 4.34 | 10.04 | 4.30 | 4.36 |
| % H$_2$O | 20.27 | 19.99 | 19.89 | 19.87 |
| % Hexylene glycol | 15.39 | 9.97 | 15.81 | 15.77 |
| Appearance of product | yellow solution | clear | clear | clear |

*diglyme is diethylene glycol dimethyl ether
DMF is N,N-dimethylformamide
DMAC is N,N-dimethylacetamide

EXAMPLES 19 – 22

The reaction may be carried out with the second step done at elevated temperatures, as illustrated by the Example 20 – 23. Using the same amounts of materials and solvents as in Example 18, the second step reactions were carried out at the temperatures shown. The effect of increasing temperature is the same as increasing the proportion of hexylene glycol, i.e. the reaction becomes faster.

TABLE IV

| Example | Temperature of Step 2 | Reaction Time |
|---|---|---|
| 20 | 30–32° | 75 min. |
| 21 | 50–53° | 20 min. |
| 22 | 75–78° | 12 min. |
| 23 | 95–100° | 10 min. |

Examination of the products by infrared spectroscopy, TLC and GLC showed them to be free of impurities.

EXAMPLE 23

Maleic anhydride (93.35 g; 0.952 mole) was dissolved in 59.8 g. tetramethylene sulfone and added through an addition funnel to N,N-dimethyl propane-1,3-diamine (97.29 g; 0.952 mole) dissolved in 156.5 g deionized water, as described in Example 3. Then 141.3 g hexylene glycol was added followed by 1,1,2,2-tetrahydroperfluoroalkylmercaptan (346 g; 0.762 mole). The system was warmed to 35° C and then allowed to exotherm to 46° C with stirring. Stirring was continued for a total of three hours while the system cooled. Gas chromatography showed that all mercaptan had reacted. The product was a clear solution consisting of:
% solids 60.0
% tetramethylene sulforn 6.7
% hexylene glycol 15.80
% water 17.50

In this example perfluoroalkyl is R$_f$ with the following composition:
C$_4$F$_9$ 1%
C$_6$F$_{13}$ 40%
C$_8$F$_{17}$ 44%
C$_{10}$F$_{21}$ 14%  C$_{12}$F$_{25}$ 1%

What we claim is:

1. A process for the preparation of a concentrated solution of fluorinated amphoteric surfactants of the formulae

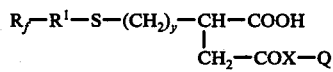

and its isomer

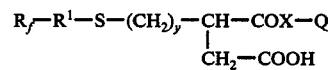

wherein
R$_f$ is straight or branched chain perfluoroalkyl of 1 to 18 carbon atoms or said perfluoroalkyl substituted by perfluoroalkoxy of 2 to 6 carbon atoms,
R$^1$ is branched or straight chain alkylene of 1 to 12 carbon atoms, alkylenethioalkylene of 2 to 12 carbon atoms, alkyleneoxyalkylene of 2 to 12 carbon atoms or alkyleneiminoalkylene of 2 to 12 carbon atoms where the nitrogen atom contains as a third substituent hydrogen or alkyl of 1 to 6 carbon atoms,
$y$ is 1 or zero,
X is oxygen or —NR, wherein R is hydrogen, lower alkyl of 1 to 6 carbon atoms, hydroxyalkyl of 1 to 6 carbon atoms, or R together with Q forms a piperazine ring, and
Q is an aliphatic amino group of the formula

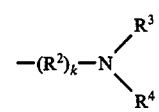

wherein
R$^2$ is a linear or branched alkylene of 2 to 12 carbon atoms, oxygen or sulfur interrupted linear or branched alkylene of up to 60 carbon atoms, or hydroxyl substituted alkylene;
$k$ is 1 or zero, with the proviso, that if X is oxygen, $k$ is 1;
R$^3$ and R$^4$ are each independently of the other an alkyl group of 1-4 carbon atoms; said process comprising
(a) reacting in a 1:1 ratio an aqueous solution of an amine with an anhydride previously dissolved in an anhydrous, non-reactive water miscible organic solvent, at a temperature of between 10° to 25° C and
(b) reacting the product obtained in the first step with an R$_f$-thiol in the presence of a non-reactive, water miscible thiol solvent, the ratio of the water miscible thiol solvent to water being such that the product is a homogeneous liquid composition.

2. A process of claim 1 wherein the anhydrous water miscible organic solvent is dimethylformamide, dimethylacetamide, or N-methylpyrrolidone, the water miscible $R_f$-thiol solvent is selected from alcohols, ketones, N-methyl pyrrolidone, dimethylformamide, acetonitrile and dioxane, the second step of the reaction being carried out at a temperature between 20° and 100° C.

3. A process of claim 2 wherein $R_f$ is straight or branched chain perfluoroalkyl of 1 to 18 carbons, $R^1$ is branched or straight chain alkylene, $y$ is 0, and X is -NR where R is methyl.

4. A process of claim 3 wherein the solvent for the anhydride is tetramethylene sulfone and the solvent for the thiol is hexylene glycol and the ratio of water to hexylene glycol is 1:0.75 to 1:1.2 parts by weight.

* * * * *